United States Patent [19]
O'Brien et al.

[11] Patent Number: 5,976,799
[45] Date of Patent: Nov. 2, 1999

[54] EARLY DETECTION OF OVARIAN CARCINOMA USING P16 GENE PRODUCTS

[75] Inventors: Timothy J. O'Brien, Little Rock, Ark.; Kazushi Shiqemasa, Hiroshima, Japan

[73] Assignee: The Board of Trustees of the University of Arkansas, Little Rock, Ak.

[21] Appl. No.: 08/819,358

[22] Filed: Mar. 17, 1997

Related U.S. Application Data

[60] Provisional application No. 60/041,554, Mar. 21, 1996.
[51] Int. Cl.$^6$ .............................. C12Q 1/68; C07H 21/04
[52] U.S. Cl. ............................................... 435/6; 536/24.3
[58] Field of Search ............................ 435/6, 69.1, 91.2; 536/24.3

[56] References Cited

PUBLICATIONS

Rodabaugh et al. Detailed deletion mapping of chromosome 9p and p16 gene alterations in human borderline and invasive epithelial ovarian tumors. Oncogene vol. 11:1249–1254, Nov. 2, 1995.

Ragione et al. 5'–deoxy–5'–methyladenosine phosphorylase and p 16(ink4) deficiency in multiple tumor cell lines. Oncogene vol. 10:827–833, Mar. 16, 1995.

Okamoto et al. p16(ink4) mutations and altered expression in human tumors and cell lines. Cold Spring Harbor Symposia on Quantitative Biology. vol. 59:49–57, 1994.

Schultz et al. Characterization of chromosome 9 in human ovarian neoplasia identifies frequent genetic imbalance on 9q and rare alterations involving 9p, including CDKN2. Cancer Res. vol. 55:2150–2157, May 15, 1995.

*Primary Examiner*—James Ketter
*Assistant Examiner*—William Sandals
*Attorney, Agent, or Firm*—Martin L. McGregor

[57] ABSTRACT

Increased expression of the p16 gene occurs early in the development of ovarian carcinomas. This invention detects change ovarian epithelium by measuring increases in p16 gene expression by a quantitative method that compares the levels of p16 mRNA and a control mRNA ($\beta$-tubulin) in a subject to be tested against the levels of substrates in normal subjects. A biological sample such as peritoneal fluid containing mRNA derived from a subject's ovarian epithelium is taken from the subject to be tested. The mRNA is isolated from the sample, and complementary cDNA is prepared from the isolated mRNA. Using primers to p16 target sequences and to $\beta$-tubulin control sequences, the cDNA is amplified. The resultant amplification products are quantitated as to p16 and $\beta$-tubulin gene sequences. The level p16 gene expression is assessed relative to expression levels in normal subjects. An increased level of p16 gene expression in a subject determined by this method is an indication of change in the subject's ovarian epithelium indicative of presence of a carcinoma.

6 Claims, 7 Drawing Sheets

EARLY DETECTION OF OVARIAN CARCINOMA USING P16 GENE PRODUCTS

RELATED APPLICATIONS

This Application claims benefit of provisional application Ser. No.: 60/041,554 Filed: Mar. 21, 1996, and abandoned by operation of law as of Mar. 21, 1997.

FIELD OF THE INVENTION

This invention is in the field of molecular biology and cancer diagnostics. More specifically, it is in the field of early detection of carcinomas of the ovarian epithelium.

BACKGROUND OF THE INVENTION

Ovarian cancer is the forth most common cause of death from cancer in women. Further, ovarian cancer is the leading cause of death among women with cancer of the female reproductive tract. As is the case with other common human carcinomas, a series of multiple genetic alterations are believed to be involved in the development of ovarian cancer. Some genetic abnormalities can alter the normal function of tumor suppressor gene products quantitatively and/or qualitatively and contribute to carcinogenesis. However, the genetic alterations involved in ovarian carcinoma remain largely unknown.

Despite the advances in imaging techniques and the availability of serum tumor markers (such as CA125), the majority of ovarian cancer patients are still diagnosed at an advanced stage of the disease—Stage III or IV. Although surgery and intensive chemotherapy have improved to a limited extent the response of ovarian cancer patients to treatment, recurrence and mortality among these patients remains a major problem. Clearly, the development of an early indicator of risk of ovarian cancer will be useful as a tool for early diagnosis and improving prognosis.

The p16 gene (or MST1 gene) has also been identified as a putative tumor suppressor gene. By binding to and inhibiting cyclin-dependent kinase (CDK4), which is activated by cyclin-D in the G1 phase of the cell cycle. It plays a critical role in regulation of normal cell growth. p16 could suppress cell division in a similar fashion to p21 by inhibiting the activity of cyclin-CDK complex. In addition, the p16 gene has already been shown on a high frequency of mutation in tumor cell lines however a much lower mutation frequency was detected in primary tumors.

SUMMARY OF THE INVENTION

An object of the present invention is a method for detecting change in the ovarian epithelium of a human subject, and especially detection of ovarian tumors and carcinomas. This may be accomplished by taking a biological sample from the subject containing a p16 gene product, such as p16 mRNA, derived from said subject's ovarian epithelium; measuring the p16 geneproduct, such as by isolating the p16 mRNA from the sample; preparing complementary cDNA to the mRNA; combining the prepared cDNA with primers complementary to p16 DNA target sequences and to a control DNA target sequences; amplifying the DNA in the sample to produce amplification products; quantitating the amplification products; and comparing the quantity of p16 target sequence amplification product in the subject's sample against the quantity of p16 target sequence amplification product from a similarly treated different sample to detect a change in the subject's ovarian epithelium relative to the different sample. The preferred p16 target sequences are about 274 bp to 546 bp long.

The different sample may be taken from the same subject that is being tested, from a subject known to have a normal ovarian epithelium, or from a subject known to have an ovarian carcinoma. The biological sample may be peritoneal fluid or any other sample that contains p16 gene product. "p16 gene product" is defined as the p16 gene itself and any of its products, or expression products, including p16 cDNA, p16 mRNA and p16 proteins.

Both internal controls (in the same reaction mixture as the sample) and external controls (in a separate reaction mixture from the sample) may be practiced in this method. Preferred control are non p16 gene products that appear at substantially the same level in both normal and tumor samples. β-tubulin represents one such control.

Measurement and quantitation may be accomplished by any of a number of means known to one skilled in the art, including gel electrophoresis, isotopic labeling and immunoassay with radioactive or other detection method.

Another object of the present invention is to provide a kit for detecting change in the ovarian epithelium of a human subject. The kit comprises a container, reagents for measuring the relative level of a p16 gene product in a biological sample. Preferably the kit will include instructions. Reagents for measuring include those for quantitating the level of a p16 gene product in a biological sample. Additionally, the kit may include a calibrated chart in which the response of the reagents to known levels of a p16 gene product is plotted, and incorporates use of a control, such as a β-tubulin gene product, as a calibration standard.

A further object of the present invention is a method for early detecting an ovarian carcinoma in a human subject. This is accomplished by taking a biological sample from said subject, the sample containing a p16 gene product derived from said subject's ovarian epithelium; isolating the p16 gene product from the sample; and measuring the p16 expression. For example isolating p16 mRNA from the sample, preparing complementary cDNA to the mRNA; combining the prepared cDNA with primers complementary to p16 DNA target sequences and to one or more control DNA target sequences; amplifying the DNA in the sample to produce amplification products; quantitating the amplification products; and comparing the quantity of p16 target sequence amplification product in the subject's sample against the quantity of p16 target sequence amplification product from a similarly treated reference sample to detect a change in the subject's ovarian epithelium relative to the reference sample. The reference sample may be taken from the group consisting of a sample from the same subject, a normal sample from a subject known to be ovarian tumor free, and a sample from a subject known to have an ovarian tumor.

Another object of the present invention is a method for producing a calibrated chart by collecting a biological sample from each member of a first group of subjects known to bear an ovarian tumor, and from each member of a second group of subjects known to be free of an ovarian tumor; quantitating the presence of a p16 gene product in each sample, the gene product selected from the group consisting of p16 cDNA, p16 mRNA and p16 protein; and then making a chart that shows the quantity of the p16 gene product for the tumor-bearing versus the tumor-free groups of subjects. The quantity of p16 target sequence amplification product in the subject's sample is compared against the calibrated chart of p16 target sequence amplification product from similarly treated normal samples to detect a change in the subject's ovarian epithelium relative to normal subjects. Alternatively, early detection of an ovarian tumor can be accomplished in a subject by comparing the quantity of p16 target sequence amplification product in the subject's sample is compared against the quantity of p16 target sequence amplification product from similarly treated samples from subjects known to have ovarian tumors. Such early detection of ovarian tumors can be accomplished by determining p16 protein expression in the sample to early detect the presence of an ovarian tumor and comparing it with the calibrated chart.

The data base for this chart will allow comparison of p16 gene product expression levels and mutation status with other possible cancer related genes in individual ovarian tumors. The relationship of gene product expression and mutation and the effect this relationship has on malignant potential can provide important insight into candidate genes which have diagnostic potential and which may be candidates for gene therapy.

While a number of objects and advantages are disclosed above, it is well within the ability of one skilled in the art, in view of the present teachings, to conceive of additional objects and advantages that are still within the scope and spirit of the invention as a whole as disclosed herein.

DETAILED DESCRIPTION OF THE INVENTION

Figure 1:
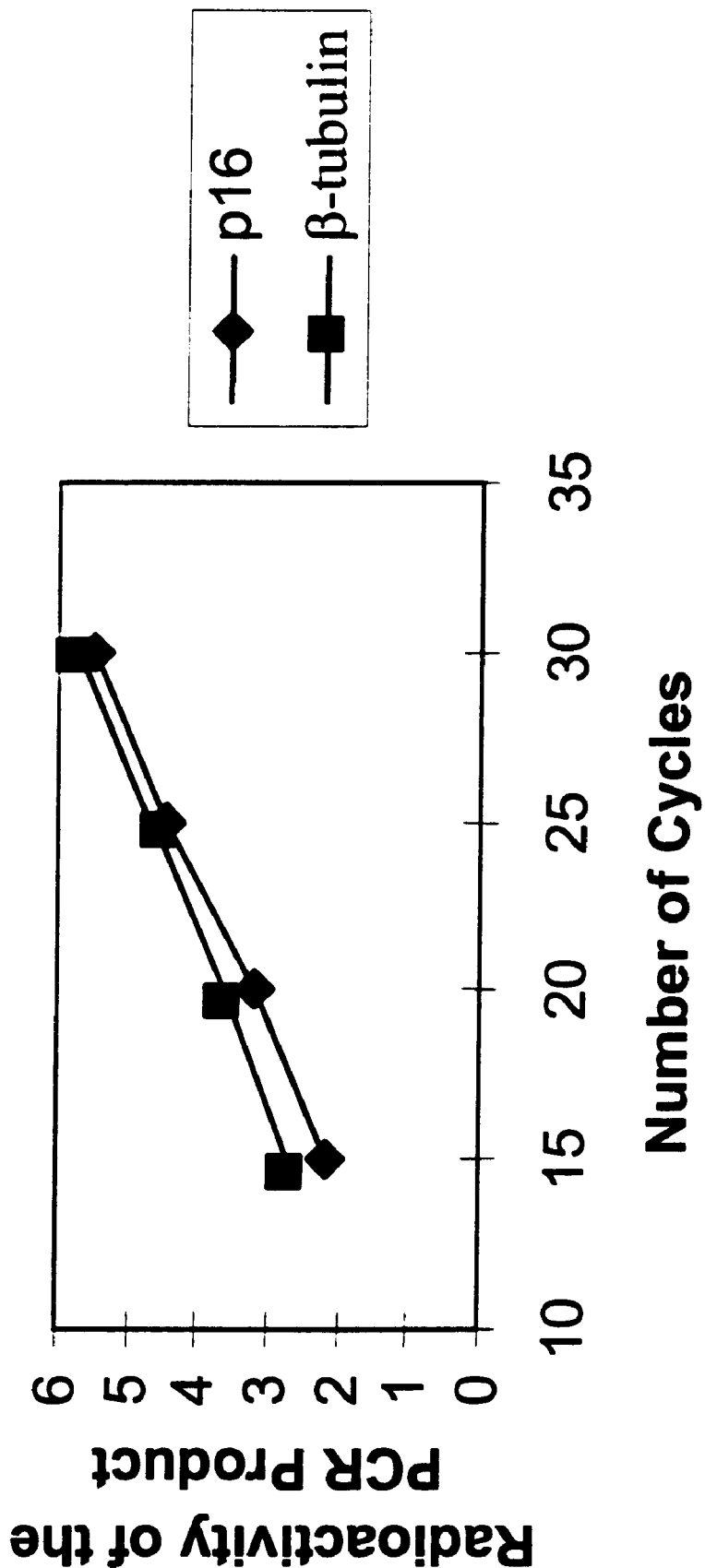
FIG. 1. Linearity of β-tubulin and the p16 amplification products out to 30 amplification cycles.

Samples:

Fresh surgical specimens of ovarian epithelial tumors were obtained from 32 subjects. They consisted of 2 benign cystadenomas, 6 cystadenomas of low malignant potential (LMP) and 24 cystadenocarcinomas. The specific tumor types studied are shown in Table 1.

TABLE I

Expression of p53, p21, and p16 Genes and Mutation of p53 and p16 Genes in Normal Ovaries and Ovarian Tumors.

| Case No. | Lab No. | Histology | mRNA Expression | | | Mutation | |
|---|---|---|---|---|---|---|---|
| | | | p53 | p21 | p16 | p53 | p16 |
| 1 | 858 | NORMAL OVARY | N | N | N | ND | ND |
| 2 | 868 | NORMAL OVARY | N | N | N | ND | WT |
| 3 | 773 | NORMAL OVARY | N | N | N | ND | ND |
| 4 | 430 | NORMAL OVARY | N | N | N | ND | WT |
| 5 | 456 | NORMAL OVARY | N | N | N | ND | ND |
| 6 | 768 | NORMAL OVARY | N | N | N | ND | WT |
| 7 | 1065 | SEROUS CYSTADENOMA | N | N | +++ | ND | WT |
| 8 | 646 | SEROUS CYSTADENOMA | N | N | N | ND | P* |
| 9 | 1031 | SEROUS CYSTADENOMA OF LMP | N | N | ++ | ND | P* |
| 10 | 481 | SEROUS CYSTADENOMA OF LMP | N | - - | ++++ | ND | WT |
| 11 | 1036 | MUCINOUS CYSTADENOMA OF LMP | N | N | ++++ | ND | WT |
| 12 | 1101 | MUCINOUS CYSTADENOMA OF LMP | - - | - - | ++++ | ND | P* |
| 13 | 919 | MUCINOUS CYSTADENOMA OF LMP | - - | - - | ++++ | MUTATED | WT |
| 14 | 794 | MUCINOUS CYSTADENOMA OF LMP | N | N | N | ND | WT |
| 15 | 1242 | SEROUS CYSTADENOCARCINOMA | ++ | - - | ++ | MUTATED | WT |
| 16 | 475 | SEROUS CYSTADENOCARCINOMA | N | - - | ++++ | ND | WT |
| 17 | 1035 | SEROUS CYSTADENOCARCINOMA | ++ | N | N | WT | WT |
| 18 | 1240 | SEROUS CYSTADENOCARCINOMA | ++ | N | ++++ | WT | WT |
| 19 | 643 | SEROUS CYSTADENOCARCINOMA | N | N | ++++ | ND | WT |
| 20 | 1041 | SEROUS CYSTADENOCARCINOMA | ++ | - - | ++++ | ND | WT |
| 21 | 1032 | SEROUS CYSTADENOCARCINOMA | N | N | N | ND | WT |
| 22 | 464 | SEROUS CYSTADENOCARCINOMA | N | - - | ++++ | ND | WT |
| 23 | 1039 | SEROUS CYSTADENOCARCINOMA | N | N | ++++ | ND | WT |
| 24 | 468 | SEROUS CYSTADENOCARCINOMA | N | - - | ++++ | ND | P* |
| 25 | 791 | SEROUS CYSTADENOCARCINOMA | N | N | ++++ | ND | WT |
| 26 | 515 | SEROUS CYSTADENOCARCINOMA | - - | - - | ++++ | MUTATED | WT |
| 27 | 1245 | SEROUS CYSTADENOCARCINOMA | N | N | ++++ | ND | WT |
| 28 | 1026 | SEROUS CYSTADENOCARCINOMA | N | N | ++++ | ND | WT |
| 29 | 1033 | SEROUS CYSTADENOCARCINOMA | ++ | - - | ++++ | MUTATED | WT |
| 30 | 465 | SEROUS CYSTADENOCARCINOMA | N | N | ++++ | ND | WT |
| 31 | 482 | SEROUS CYSTADENOCARCINOMA | - - | ++ | ++++ | WT | WT |
| 32 | 1243 | MUCINOUS CYSTADENOCARCINOMA | | N | ++++ | ND | WT |
| 33 | 484 | MUCINOUS CYSTADENOCARCINOMA | | - - | ++++ | MUTATED | WT |

TABLE I-continued

Expression of p53, p21, and p16 Genes and Mutation of p53 and p16 Genes in Normal Ovaries and Ovarian Tumors.

| Case No. | Lab No. | Histology | mRNA Expression | | | Mutation | |
|---|---|---|---|---|---|---|---|
| | | | p53 | p21 | p16 | p53 | p16 |
| 34 | 1244 | MUCINOUS CYSTADENOCARCINOMA | N | - - | ++++ | ND | WT |
| 35 | 1246 | MUCINOUS CYSTADENOCARCINOMA | ++ | N | ++++ | WT | WT |
| 36 | 480 | ENDOMETRIOID ADENOCARCINOMA | - - | - - | ++++ | MUTATED | WT |
| 37 | 474 | CLEAR CELL CARCINOMA | N | N | ++++ | ND | WT |
| 38 | 473 | CLEAR CELL CARCINOMA | N | N | ++++ | ND | WT |

Normal range is equal to Mean ± 2SD
++ Positive is equal to Mean + 2SD to + 4SD
- - Negative is equal to Mean - 2SD to - 4SD
++++ Positive is equal to Mean + 4SD or greater
ND, not done
WT, wild type
*, Known polymorphism Clinical staging was determined according to the criteria of the International Federation of Gynecology and Obstetrics. Normal ovaries were obtained from 6 patients who underwent surgery for benign gynecological disease.

mRNA Isolation:

mRNA was prepared from the samples using a RIBOSEP™ mRNA isolation kit (Becton Dickson Laboratories). The amount of mRNA recovered was quantitated by UV spectrophotometry.

cDNA Synthesis:

Complementary DNA was synthesized from 1.0 ug of mRNA by random hexamer priming using a 1ST STRAND™ cDNA synthesis kit (CLONTECH). The efficiency of the cDNA synthesis was estimated by using CLONTECH's positive control amplimer (G3PDH). The target sequences were amplified in parallel with the B-tubulin genes as an internal control. Primers used for amplification were designed to yield different sized products between 274 bp–546 bp. For quantitation, 2–5 µCi of $^{32}$PdCTP was added to the amplification reaction mixture. Amplification products were separated on 2% agarose gels and the radioactivity of each product was determined using PHOSPHO IMAGER™ (Molecular Dynamics). Amplification products for sequencing were also prepared and direct sequencing was performed on them.

Quantitative Amplification:

Amplification was accomplished using Polymerase Chain Reaction (PCR) chemistry in a Thermal Cycler (Perkin-Elmer Cetus) with the reaction mixture consisting of cDNA derived from 50 ηg of mRNA, 5 ρmol of sense and antisense primers for both the target gene and the β-tubulin gene, 200 µmol of dNTPs, 2–5 µCI of α-$^{32}$ PdCTP and 0.25 units of Taq DNA polymerase in reaction buffer (Promega in a final volume of 25 µl. The primer sequences are listed in Table 2. The target sequences were amplified in parallel with the β-tubulin gene as an internal control. Each cycle of amplification included 30 seconds of denaturation at 95 degrees, 1 minute of primer annealing at 62 degrees and 1 minute of extension at 72 degrees. Thirty cycles of PCR were performed and the products were separated on 2% agarose gel. The radioactivity of each band were determined by PHOSPHO IMAGER™ (Molecular Dynamics). Initial studies showed linearity of incorporation for B-tubulin and the target genes over 30 cycles.

TABLE 2

Sequences of amplification Primers Used for Quantitative PCR

| GENE | | | PRIMER |
|---|---|---|---|
| p53 | 4A (SEQ. ID. NO. 1) | SENSE | 5-AGGCGCTGCCCCCACCA-3 |
| | 4B (SEQ. ID. NO. 2) | ANTISENSE | 5-TTCCGTCCCAGTAGATT-3 |
| p21 | 1A (SEQ. ID. NO. 3) | SENSE | 5-GCCGAAGTCAGTTCCTT-3 |
| | 2B (SEQ. ID. NO. 4) | ANTISENSE | 5-TCATGCTGGTCTGCCGC-3 |
| p16 | 4A (SEQ. ID. NO. 5) | SENSE | 5-CCCCACTACCGTAAATG-3 |
| | 4B (SEQ. ID. NO. 6) | ANTISENSE | 5-GAGCTTTGGTTCTGCCA-3 |
| β-TUBULIN | (SEQ. ID. NO. 7) | SENSE | 5-TGCATTGACAACGAGGC-3 |
| | (SEQ. ID. NO. 8) | ANTISENSE | 5-CTGTCTTGACATTGTTG-3 |

Each sense primers have Hind3 linker sequences (GCAAGCTT) and each antisense primers have Kpn1 linker sequences (GCGGTACC) on 5 primer ends.

Direct Sequencing:

PCR amplification was carried out using the primers listed in Table 3. Amplification products were purified using WIZARD™ PCR Preps DNA Purification System (Promega). The sequencing reaction was carried out using a PRISM™ Ready Reaction DyeDeoxy Terminator Cycle Sequencing Kit (Applied Biosystems). To remove the excess DyeDeoxy terminators, the completed sequencing reaction was purified using a CENTRI-SEP™ spin column (Princeton Separation). An Applied Biosystems Model 373A DNA Sequencing System was used for direct sequence determination.

TABLE 3

Sequences of Amplification Primers Used for Direct Sequencing

| GENE | | | PRIMER |
|---|---|---|---|
| p53 | 3A | (SEQ. ID. NO. 9) | SENSE | 5-CTGGCCCCTGTCATCTT-3 |
| | 3B | (SEQ. ID. NO. 10) | ANTISENSE | 5-TATCTGACAGCGCTCA-3 |
| | 4A | (SEQ. ID. NO. 11) | SENSE | 5-AGGCGCTGCCCCCACCA-3 |
| | 4B | (SEQ. ID. NO. 12) | ANTISENSE | 5-TTCCGTCCCAGTAGATT-3 |
| | 5A | (SEQ. ID. NO. 13) | SENSE | 5-TGGAAGACTCCAGTGGT-3 |
| | 5B | (SEQ. ID. NO. 14) | ANTISENSE | 5-CTTGAGTTCCAAGGCCT-3 |
| p16 | 1A | (SEQ. ID. NO. 15) | SENSE | 5-CGCACCGAATAGTTACG-3 |
| | 1B | (SEQ. ID. NO. 16) | ANTISENSE | 5-CCAGCGTGTCCAGGAAG-3 |
| | 2A | (SEQ. ID. NO. 17) | SENSE | 5-CTTCCTGGACACGCTGG-3 |
| | 2B | (SEQ. ID. NO. 18) | ANTISENSE | 5-CTGTAGGACCTTCGGTG-3 |

Each sense primers have Hind3 linker sequences (GCAAGCTT) and each antisense primers have Kpn1 linker sequences (GCGGTACC) on 5 primer ends.

p53 sequence covers from aa 90 to aa 351 (sequence goes from the middle of exon 4 to the middle of exon 10).

p16 sequence covers from aa 40 to terminal amino acid (sequence goes from middle of exon 1 through the end of exon 3).

Figure 2:
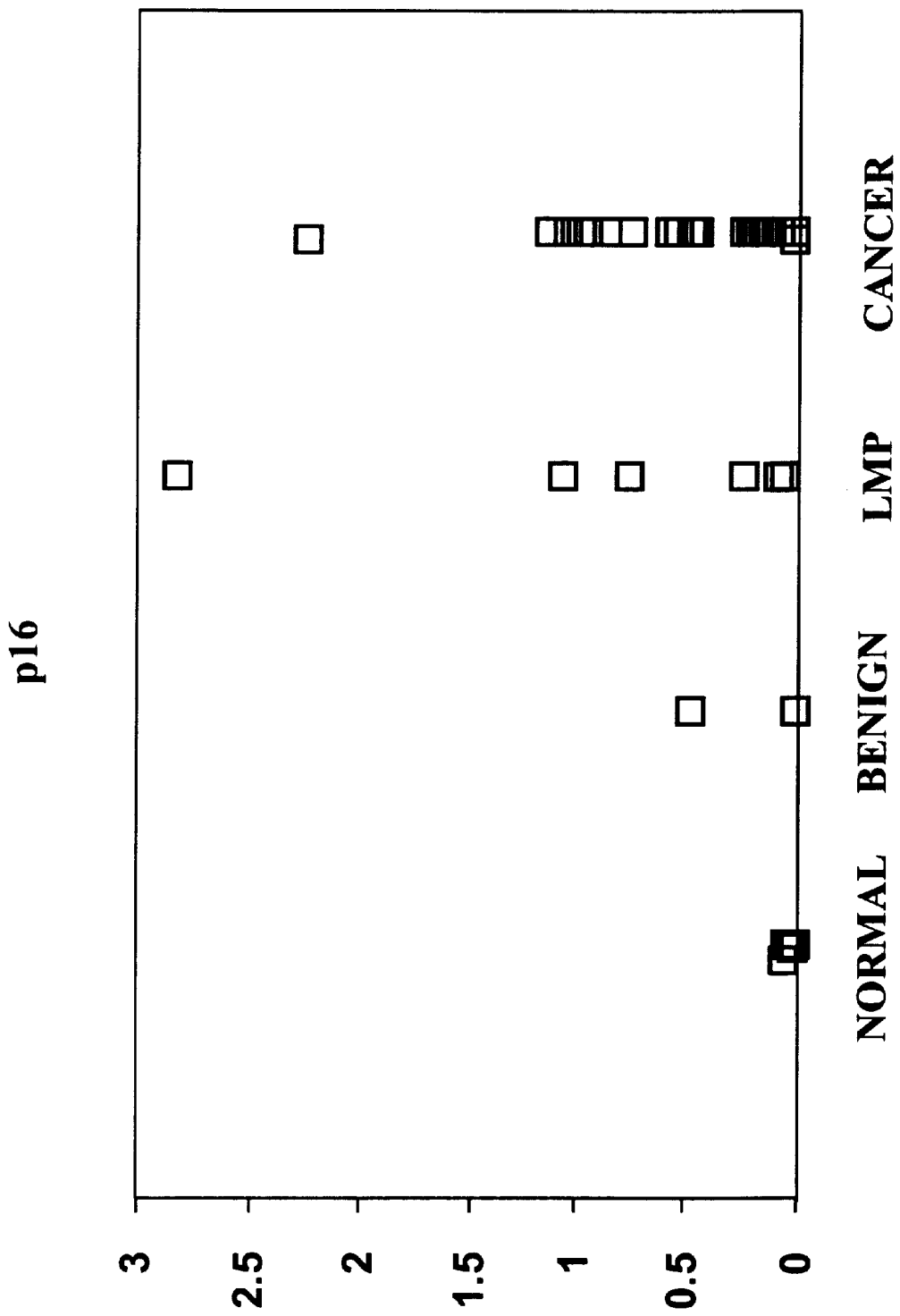
FIG. 2. p16 expression relative to β-tubulin in normal ovary, benign ovarian tumor, LMP tumor and ovarian cancer. p16 expression is significantly elevated in many ovarian tumor cases.
Figure 3:
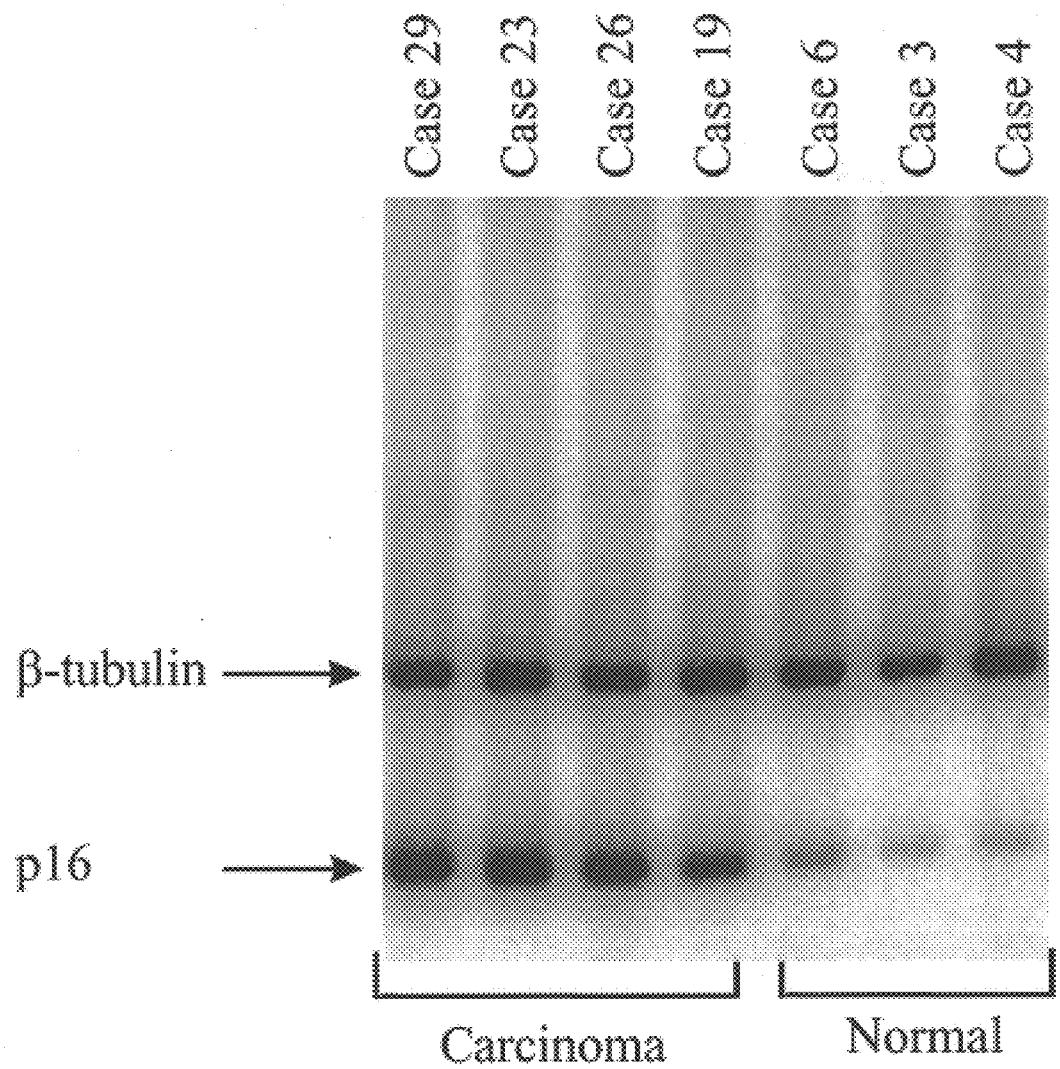
FIG. 3. p16 and β-tubulin PCR amplification products from normal ovary and ovarian cancer. Case 4, Case 3 and Case 6 are normal ovaries. Case 19, Case 26, Case 23 and Case 29 are ovarian cancers. p16 expression relative to β-tubulin is higher in cancer cases than in normal ovary cases.
Figure 4:
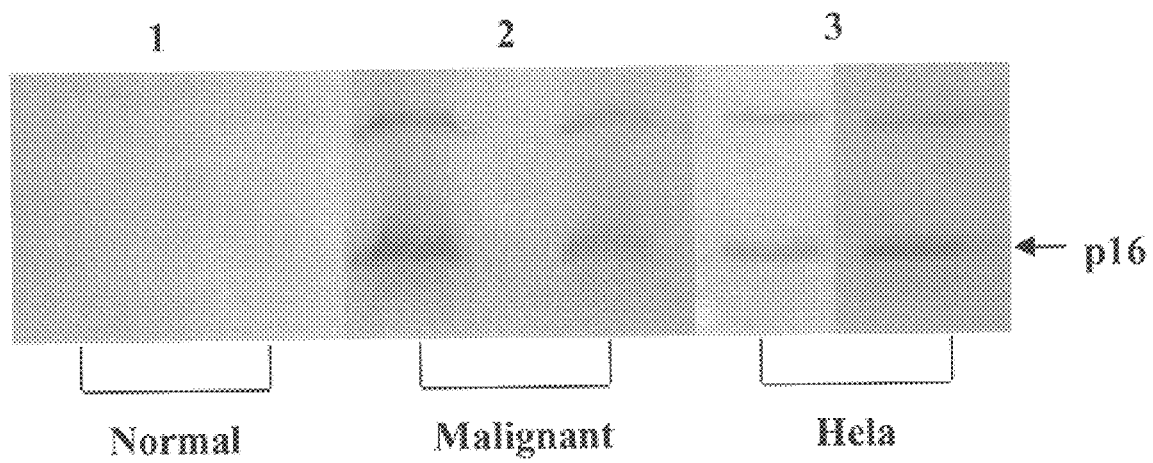
FIG. 4. Western blot analysis of p16 protein. Lane 1 is normal ovary, lane 2 is ovarian cancer Case 27 showing p16 over expression, and lane 3 is a Hela cell line as a positive control. P16 protein is strongly positive in the ovarian carcinoma case and the Hela cell line, but negative in the normal ovary sample.

Results:

mRNA expression levels of P53, p21, and p16 genes relative to B-tubulin gene are shown in Table 1, FIG. 1, FIG. 2 and FIG. 3. Cases with overexpression p16 are shown in Table 4. The expression levels of p53 relative to B-tubulin were higher in 7 ovarian cancer cases and lower in 4 cases. p53 levels were also lower in 2 low malignant potential tumors. The expression levels of p53 relative to β-tubulin were higher in some ovarian cancer cases compared to normal ovaries. p21 expression levels of tumor were often lower than that of normal ovaries. In contrast to the fluctuation of results observed with p53 expression, p16 expression is more consistently significantly elevated in many ovarian cancer cases including some cases where p53 is mutated. Some tumors showed elevated p53 expression, low p21 expression and high p16 expression.

TABLE IV

Overexpression of p16 in Ovarian Carcinoma

| | N | p16 + 2SD or greater |
|---|---|---|
| Normal ovary | 6 | 0 (0%) |
| Benign tumor | 2 | 1 (50%) |
| LMP | 6 | 5 (83%) |
| Carcinoma Stage | 24 | 32 (92%) |
| stage 1/2 | 4 | 3 (75%) |
| stage 3/4 | 20 | 19 (95%) |
| Type | | |
| serous | 17 | 15 (88%) |
| mucinous | 4 | 4 (100%) |

TABLE IV-continued

Overexpression of p16 in Ovarian Carcinoma

| | N | p16 + 2SD or greater |
|---|---|---|
| endomtrioid | 1 | 1 (100%) |
| clear cell | 2 | 2 (100%) | p21 expression levels were lower in 3 LMP tumors and in 10 ovarian cancer cases than that of normal ovaries. One ovarian cancer case showed higher p21 expression (Case 31). p16 expression was significantly elevated in 28 of 32 tumors studied. Normal levels of p16 were found in only one serous adenoma, one mucinous adenoma of LMP and 2 serous carcinomas.

Figure 5:
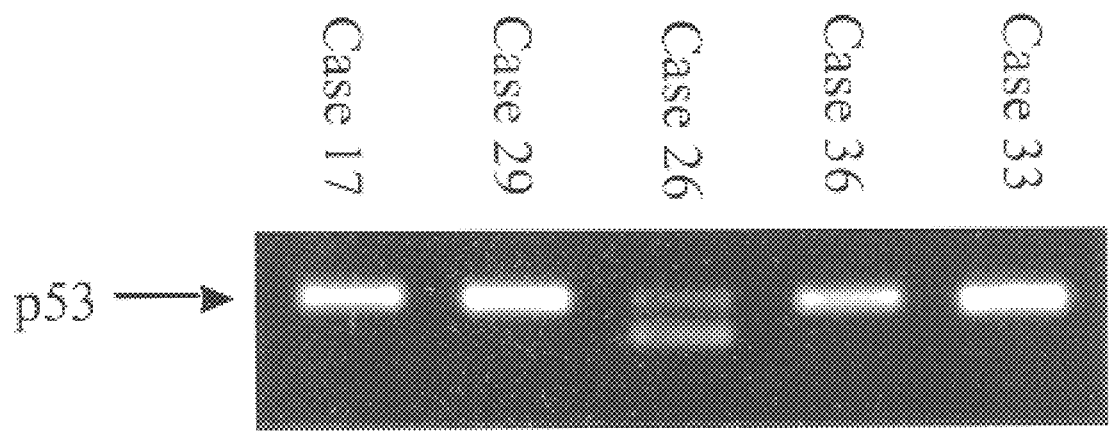
FIG. 5. p16 PCR product prepared for direct sqencing.
Figure 6:
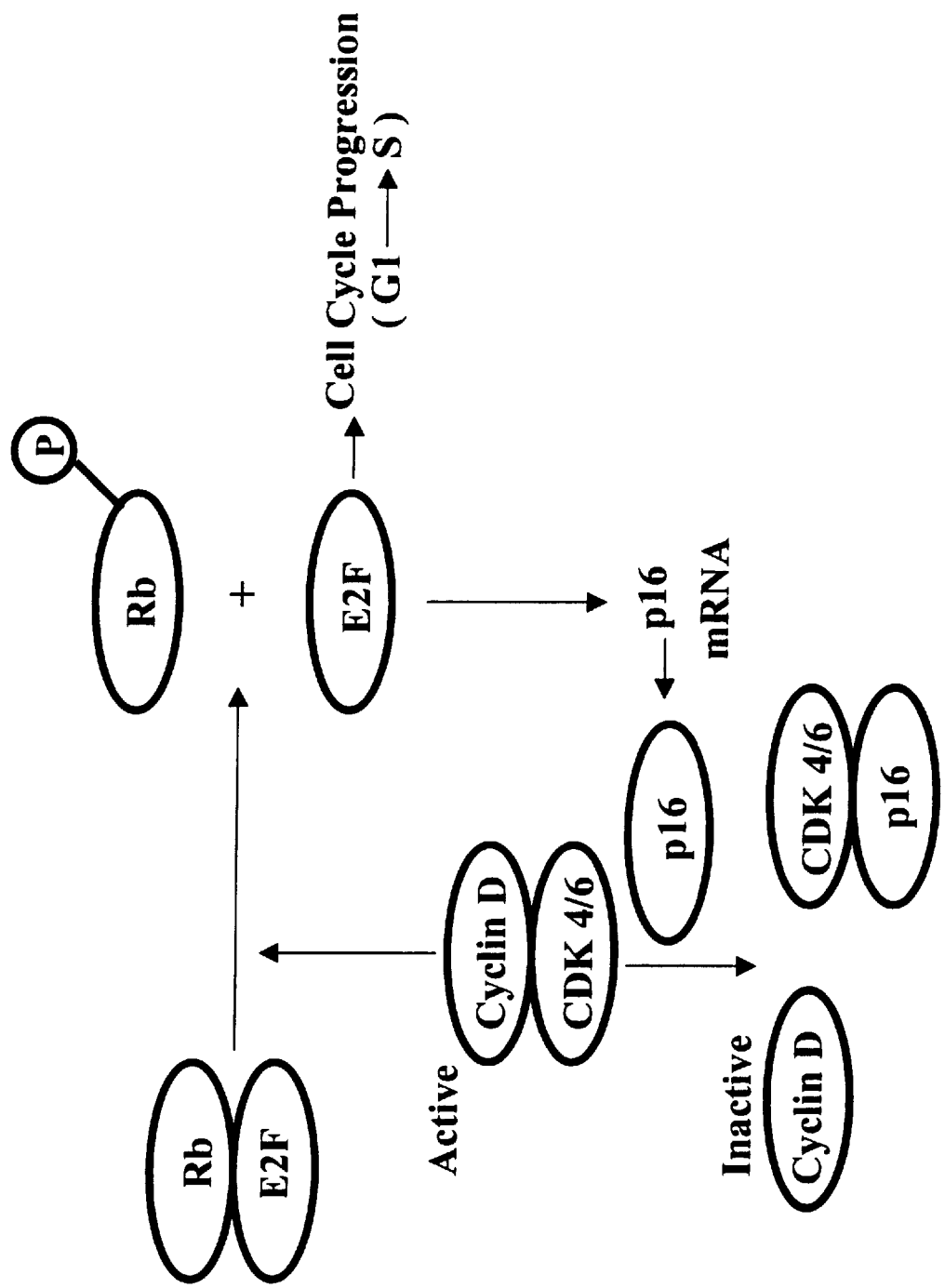
FIG. 6. Cyclin D and CDK4/6 stimulate cell division by phosphorylating retinoblastoma (Rb) protein. A transcription factor such as E2F is released and activates the transition from B1 to S phase of the cell cycle. p16 binds the catalytic subunit CDK4 or CDK6 and inactivates the Cyclin D - CDK4/6 complex. E2F is released from Rb and also activates the transcription of p16.
Figure 7:
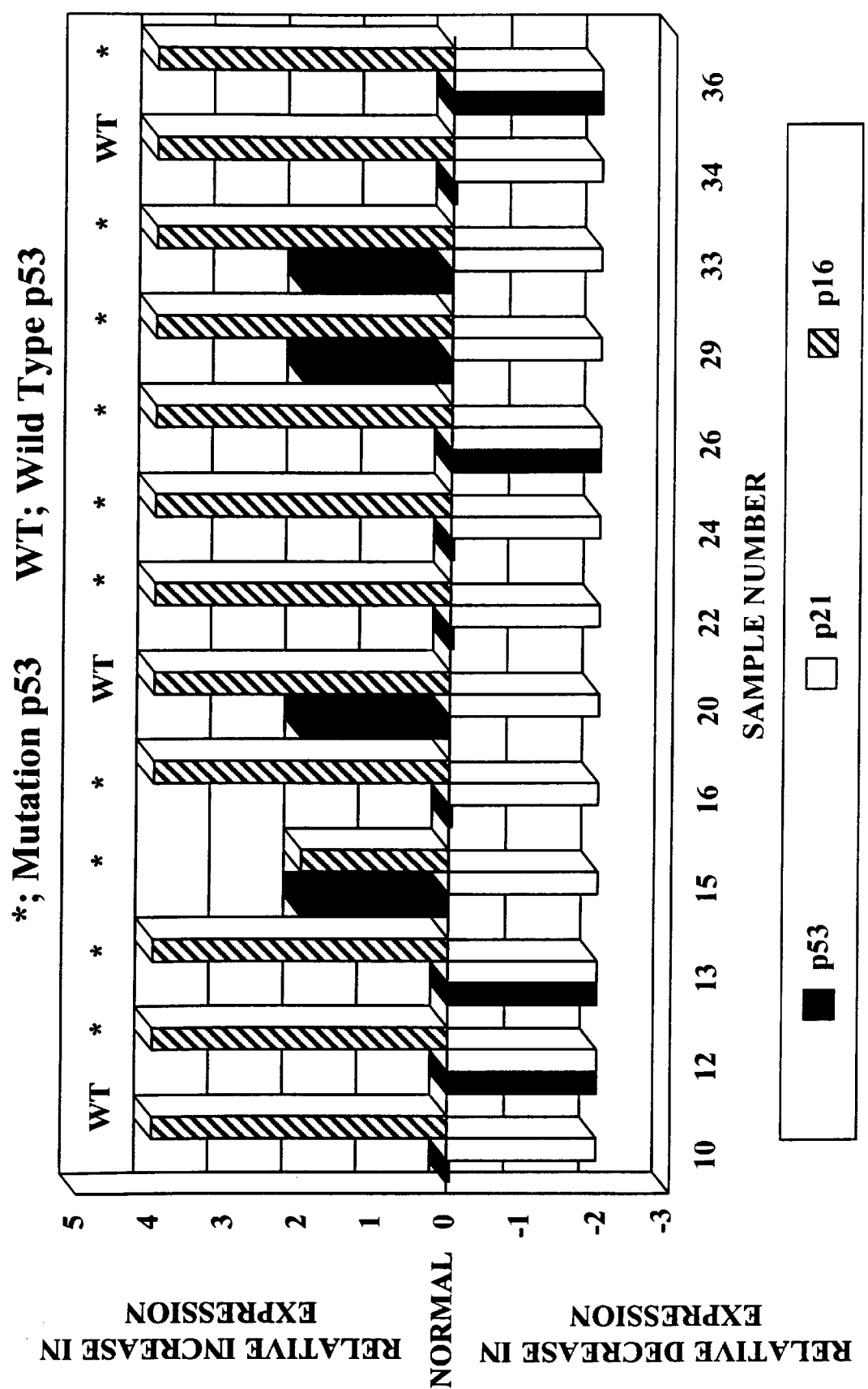
FIG. 7. Expression levels of p53, p21 and p16 and p53 mutation status.

Out of the 13 ovarian tumor cases with over expression or under expression of p53, six p53 mutated cases were found and all 6 cases resulted in amino acid changes (Table 1). According to the quantitative PCR data, 3 out of these 6 cases showed over-expression of p53 and 3 cases showed under expression of p53. In addition to that, all 6 cases showed p21 under expression (FIG. 7). One ovarian cancer (Case 33) showed one extra p53 band as well as the expected sized band (FIG. 2). The expected sized product had a T to A transversion in codon 206. The larger sized product had a G to A transition at the 3' splicing site of intron 7 that resulted in intron 7 insertion. Ovarian cancer case #26 showed one extra p53 product as well as the expected sized p53 product (FIG. 5). The smaller sized product had a 58 bp deletion from codon 106 to codon 125 resulting in a stop codon at codon 150.

Only four p16 mutated cases were found in the 32 ovarian tumor cases we examined (Tables 1 & 5). One benign ovarian tumor (Case 8) showed a G to T transversion in codon 127 and this transversion had been described as a polymorphism. Both one LMP tumor (Case 9) and one ovarian cancer (Case 24) showed the same G to A

TABLE V

Ovarian Tumors with p16 Polymorphisms

| Case No. | Tumor Type | FIGO Stage | Exon | Codon | Base Change | Amino Acid Change |
|---|---|---|---|---|---|---|
| 8 | S CYSTADENOMA | | EXON2 | aa127[a] | GCA—TCA | Ala—Ser |
| 9 | S CYSTADENOMA (LMP) | 1 | EXON2 | aa148[b] | GCG—ACG | Ala—Thr |

TABLE V-continued

Ovarian Tumors with p16 Polymorphisms

| Case No. | Tumor Type | FIGO Stage | Exon | Codon | Base Change | Amino Acid Change |
|---|---|---|---|---|---|---|
| 12 | M CYSTADENOMA (LMP) | 1 | EXON2 | aa68 | GCG—GCA | No Change |
| 24 | S CARCINOMA | 3 | EXON2 | aa148[b] | GCG—ACG | Ala—Thr |

[a]G—T transversion in codon 127 has been described as polymorphism.
[b]G—A transition in codon 148 has been described as polymorphism.
S; Serous
M; Mucinous transition in codon 148 and this transition has also been described as a prevalent polymorphism. Excluding these three cases, the only p16 mutation was found in an LMP tumor (Case 12) in which a G to A transition in codon 68 was noted. This mutation however did not result in amino acid change. These data indicate that p16 expression was significantly elevated in 28 out of 32 ovarian tumor cases tested. p16 is seldom mutated in ovarian tumors. These data indicate that elevation in p16 expression is a direct positive indication of changes in the epithelium characteristic of ovarian carcinomas. Detection of p16 gene products in fluid samples is an especially sensitive means for early detection of changes in the ovarian epithelium.

While the above description contains many specificities, these should not be construed as limitations on the scope of the invention, but rather as an exemplification of one preferred embodiment thereof. Many other variation are possible, which would be obvious to one skilled in the art. Accordingly, the scope of the invention should be determined by the scope of the appended claims and their legal equivalents, and not just by the embodiments.

We claim:

1. A method for early detecting an ovarian carcinoma in a subject comprising the steps of:
   taking a biological sample from said subject, the sample containing a p16 mRNA derived from said subject's ovarian epithelium;
   isolating the p16 mRNA from the sample;
   preparing complementary cDNA to the p16 mRNA;
   combining the prepared cDNA with primers complementary to p16 DNA target sequences and to a control DNA target sequences;
   amplifying the DNA in the sample to produce amplification products;
   quantitating the amplification products; and
   comparing the quantity of p16 target sequence amplification product in the subject's sample against the quantity of p16 target sequence amplification product from a similarly treated reference sample to detect a change in the subject's ovarian epithelium relative to the reference sample.

2. The method of claim 1 wherein the reference sample is taken from the group consisting of a sample from the same subject, a normal sample from a subject known to be ovarian tumor free, and a sample from a subject known to have an ovarian tumor.

3. The method of claim 1 where in the comparing step, the quantity of p16 target sequence amplification product in the subject's sample is compared against a calibrated chart of p16 target sequence amplification product from similarly treated normal samples to detect a change in the subject's ovarian epithelium relative to normal subjects.

4. The method of claim 1 for the early detection of an ovarian tumor in a subject where in the comparing step, the quantity of p16 target sequence amplification product in the subject's sample is compared against the quantity of p16 target sequence amplification product from a similarly treated samples from subjects known to have ovarian tumors.

5. A method for producing a calibrated chart comprising the steps of:

collecting a biological sample from each member of a first group of subjects known to bear an ovarian tumor, and from each member of a second group of subjects known to be free of an ovarian tumor; and quantitating the presence of a p16 gene product in each sample, the gene product selected from the group consisting of p16 cDNA, p16 mRNA and p16 protein; and making a chart that shows the quantity of the p16 gene product for the tumor-bearing versus the tumor-free groups of subjects.

6. A method for early detection of ovarian tumors comprising the steps of:

collecting a sample from a subject to be tested for the presence of an ovarian tumor; and determining p16 protein expression in the sample to early detect the presence of an ovarian tumor.

* * * * *

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 17 BASE PAIRS
      (B) TYPE:  NUCLEIC ACID
      (C) STRANDEDNESS:  SINGLE
      (D) TOPOLOGY:  LINEAR (ii) MOLECULE TYPE:  OTHER NUCLEIC ACID (iii) HYPOTHETICAL:  NO (iv) ANTI-SENSE:  NO (xi) SEQUENCE DESCRIPTION: SEQ ID NO: 1:

AGGCGCTGCC CCCACCA                              17

(2) INFORMATION FOR SEQ ID NO: 2:

(i) SEQUENCE CHARACTERISTICS:
      (A) LENGTH: 17 BASE PAIRS
      (B) TYPE:  NUCLEIC ACID
      (C) STRANDEDNESS:  SINGLE
      (D) TOPOLOGY:  LINEAR (ii) MOLECULE TYPE:  OTHER NUCLEIC ACID (iii) HYPOTHETICAL:  NO (iv) ANTI-SENSE:  YES (xi) SEQUENCE DESCRIPTION: SEQ ID NO: 2:

TTCCGTCCCA GTAGATT                              17

(2) INFORMATION FOR SEQ ID NO: 3:

(i) SEQUENCE CHARACTERISTICS:
            (A) LENGTH: 17 BASE PAIRS
            (B) TYPE: NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 3:

CCGAAGTCA GTTCCTT                                                         17

(2) INFORMATION FOR SEQ ID NO: 4:

(i) SEQUENCE CHARACTERISTICS:
            (A) LENGTH: 17 BASE PAIRS
            (B) TYPE: NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: YES (xi) SEQUENCE DESCRIPTION: SEQ ID NO: 4:

TCATGCTGGT CTGCCGC                                                        17

(2) INFORMATION FOR SEQ ID NO: 5:

(i) SEQUENCE CHARACTERISTICS:
            (A) LENGTH: 17 BASE PAIRS
            (B) TYPE: NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 5:

CCCCACTACC GTAAATG                                                        17

(2) INFORMATION FOR SEQ ID NO: 6:

(i) SEQUENCE CHARACTERISTICS:
            (A) LENGTH: 17 BASE PAIRS
            (B) TYPE: NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: YES (xi) SEQUENCE DESCRIPTION: SEQ ID NO: 6:

GAGCTTTGGT TCTGCCA                                                        17

(2) INFORMATION FOR SEQ ID NO: 7:

(i) SEQUENCE CHARACTERISTICS:
            (A) LENGTH: 17 BASE PAIRS
            (B) TYPE: NUCLEIC ACID (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 7:

TGCATTGACA ACGAGGC                                                17

(2) INFORMATION FOR SEQ ID NO: 8:

(i) SEQUENCE CHARACTERISTICS:
            (A) LENGTH: 17 BASE PAIRS
            (B) TYPE: NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: YES (xi) SEQUENCE DESCRIPTION: SEQ ID NO: 8:

CTGTCTTGAC ATTGTTG                                                17

(2) INFORMATION FOR SEQ ID NO: 9:

(i) SEQUENCE CHARACTERISTICS:
            (A) LENGTH: 17 BASE PAIRS
            (B) TYPE: NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 9:

CTGGCCCCTG TCATCTT                                                17

(2) INFORMATION FOR SEQ ID NO: 10:

(i) SEQUENCE CHARACTERISTICS:
            (A) LENGTH: 17 BASE PAIRS
            (B) TYPE: NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: YES (xi) SEQUENCE DESCRIPTION: SEQ ID NO: 10:

TATCTGAGCA GCGCTCA                                                17

(2) INFORMATION FOR SEQ ID NO: 11:

(i) SEQUENCE CHARACTERISTICS:
            (A) LENGTH: 17 BASE PAIRS
            (B) TYPE: NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 11:

AGGCGCTGCC CCCACCA                                                          17

(2) INFORMATION FOR SEQ ID NO: 12:

(i) SEQUENCE CHARACTERISTICS:
            (A) LENGTH: 17 BASE PAIRS
            (B) TYPE: NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: YES (xi) SEQUENCE DESCRIPTION: SEQ ID NO: 12:

TTCCGTCCCA GTAGATT                                                          17

(2) INFORMATION FOR SEQ ID NO: 13:

(i) SEQUENCE CHARACTERISTICS:
            (A) LENGTH: 17 BASE PAIRS
            (B) TYPE: NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: NO (xi) SEQUENCE DESCRIPTION: SEQ ID NO: 13:

TGGAAGACTC CAGTGGT                                                          17

(2) INFORMATION FOR SEQ ID NO: 14:

(i) SEQUENCE CHARACTERISTICS:
            (A) LENGTH: 17 BASE PAIRS
            (B) TYPE: NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: YES (xi) SEQUENCE DESCRIPTION: SEQ ID NO: 14:

CTTGAGTTCC AAGGCCT                                                          17

(2) INFORMATION FOR SEQ ID NO: 15:

(i) SEQUENCE CHARACTERISTICS:
            (A) LENGTH: 17 BASE PAIRS
            (B) TYPE: NUCLEIC ACID
            (C) STRANDEDNESS: SINGLE
            (D) TOPOLOGY: LINEAR (ii) MOLECULE TYPE: OTHER NUCLEIC ACID (iii) HYPOTHETICAL: NO (iv) ANTI-SENSE: NO

```
        (xi) SEQUENCE DESCRIPTION: SEQ ID NO: 15:

CGCACCGAAT AGTTACG                                                              17

(2) INFORMATION FOR SEQ ID NO: 16:

(i) SEQUENCE CHARACTERISTICS:
            (A) LENGTH: 17 BASE PAIRS
            (B) TYPE:  NUCLEIC ACID
            (C) STRANDEDNESS:  SINGLE
            (D) TOPOLOGY:  LINEAR (ii) MOLECULE TYPE:  OTHER NUCLEIC ACID (iii) HYPOTHETICAL:  NO (iv) ANTI-SENSE:  YES (xi) SEQUENCE DESCRIPTION: SEQ ID NO: 16:

CCAGCGTGTC CAGGAAG                                                              17

(2) INFORMATION FOR SEQ ID NO: 17:

(i) SEQUENCE CHARACTERISTICS:
            (A) LENGTH: 17 BASE PAIRS
            (B) TYPE:  NUCLEIC ACID
            (C) STRANDEDNESS:  SINGLE
            (D) TOPOLOGY:  LINEAR (ii) MOLECULE TYPE:  OTHER NUCLEIC ACID (iii) HYPOTHETICAL:  NO (iv) ANTI-SENSE:  NO (xi) SEQUENCE DESCRIPTION: SEQ ID NO: 17:

CTTCCTGGAC ACGCTGG                                                              17

(2) INFORMATION FOR SEQ ID NO: 18:

(i) SEQUENCE CHARACTERISTICS:
            (A) LENGTH: 17 BASE PAIRS
            (B) TYPE:  NUCLEIC ACID
            (C) STRANDEDNESS:  SINGLE
            (D) TOPOLOGY:  LINEAR (ii) MOLECULE TYPE:  OTHER NUCLEIC ACID (iii) HYPOTHETICAL:  NO (iv) ANTI-SENSE:  YES (xi) SEQUENCE DESCRIPTION: SEQ ID NO: 18:

CTGTAGGACC TTCGGTG                                                              17
```